United States Patent
Polster

(10) Patent No.: US 11,723,688 B2
(45) Date of Patent: Aug. 15, 2023

(54) APPARATUS AND METHOD FOR USE OF AN INCLINOMETER-AIDED NEEDLE GUIDE

(71) Applicant: Joshua M. Polster, Shaker Heights, OH (US)

(72) Inventor: Joshua M. Polster, Shaker Heights, OH (US)

(73) Assignee: Joshua M. Polster, Shaker Heights, OH (US)

( * ) Notice: Subject to any disclaimer, the term of this patent is extended or adjusted under 35 U.S.C. 154(b) by 399 days.

(21) Appl. No.: 17/088,743

(22) Filed: Nov. 4, 2020

(65) Prior Publication Data

US 2021/0106354 A1 Apr. 15, 2021

Related U.S. Application Data

(62) Division of application No. 15/967,358, filed on Apr. 30, 2018, now Pat. No. 10,842,528.

(60) Provisional application No. 62/492,628, filed on May 1, 2017.

(51) Int. Cl.
| | |
|---|---|
| *A61B 17/34* | (2006.01) |
| *A61B 34/10* | (2016.01) |
| *A61B 34/20* | (2016.01) |
| *G01C 9/02* | (2006.01) |

(Continued)

(52) U.S. Cl.
CPC .......... *A61B 17/3403* (2013.01); *A61B 34/10* (2016.02); *A61B 34/20* (2016.02); *A61B 90/11* (2016.02); *G01C 9/02* (2013.01); *A61B 2017/3407* (2013.01); *A61B 2017/3411* (2013.01); *A61B 2034/107* (2016.02); *A61B 2034/2048* (2016.02); *A61B 2090/067* (2016.02)

(58) Field of Classification Search
CPC . A61B 5/6898; A61B 90/06; A61B 2090/061; A61B 2090/062; A61B 2090/063; A61B 2090/064; A61B 2090/067; A61B 17/3403; A61B 2017/3407; A61B 2090/068; A61B 2562/0219; A61B 1/00124; A61B 34/10; A61B 34/20; A61B 5/1071; A61B 2017/3411; A61B 2034/107; A61B 2034/2048; A61B 90/11; G01C 9/02; G01B 11/14; G01B 11/26; G03B 17/48

See application file for complete search history.

(56) References Cited

U.S. PATENT DOCUMENTS

| | | |
|---|---|---|
| 6,574,808 B1 | 6/2003 | Brown et al. |
| 2012/0191038 A1 | 7/2012 | Gerber |

(Continued)

*Primary Examiner* — Katherine M Shi
(74) *Attorney, Agent, or Firm* — Tarolli, Sundheim, Covell & Tummino L.L.P.

(57) ABSTRACT

A system, method, and apparatus for guiding a needle into a target location of a patient's body are provided. The system includes a planned needle guide trajectory and a guide for removable attachment to a smartphone. The guide includes at least one needle guiding aperture extending substantially perpendicularly to a screen of the smartphone. The needle guiding aperture defines an actual needle guide trajectory. An inclinometer application is running on the smartphone. The inclinometer application indicates to a user conformance of the actual needle guide trajectory to the planned needle guide trajectory.

9 Claims, 11 Drawing Sheets

(51) Int. Cl.
*A61B 90/11* (2016.01)
*A61B 90/00* (2016.01)

(56) References Cited

U.S. PATENT DOCUMENTS

| | | | |
|---|---|---|---|
| 2012/0320340 A1* | 12/2012 | Coleman, III | A61B 3/10 |
| | | | 351/208 |
| 2014/0257319 A1 | 9/2014 | Polster | |
| 2017/0303857 A1 | 10/2017 | Perkins et al. | |
| 2017/0311875 A1 | 11/2017 | Ludewig et al. | |

* cited by examiner

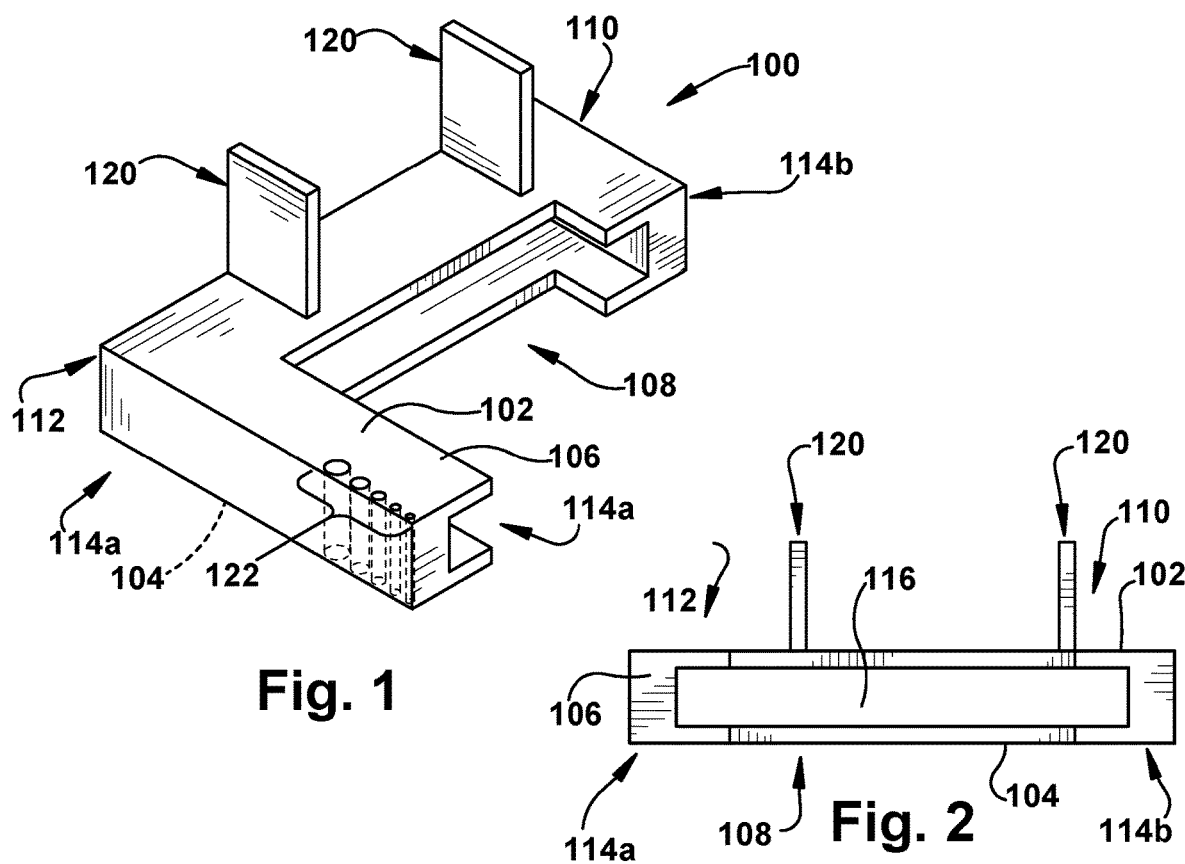
Fig. 1
Fig. 2
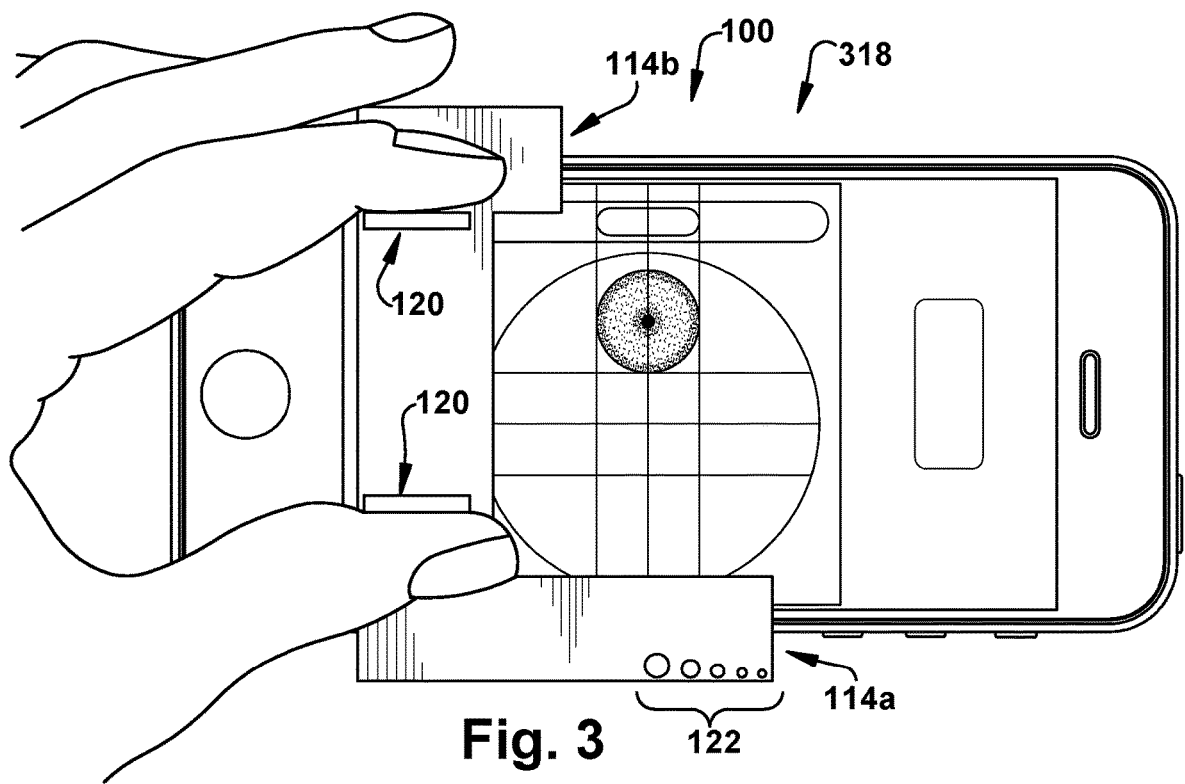
Fig. 3

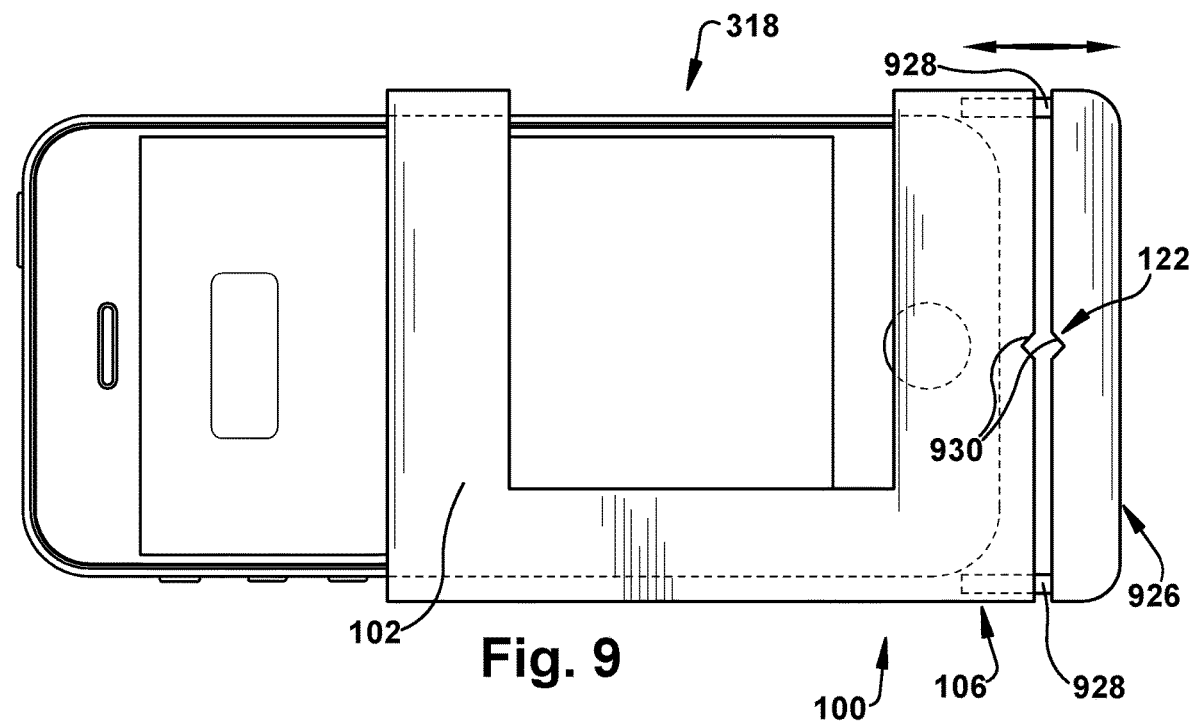
Fig. 9
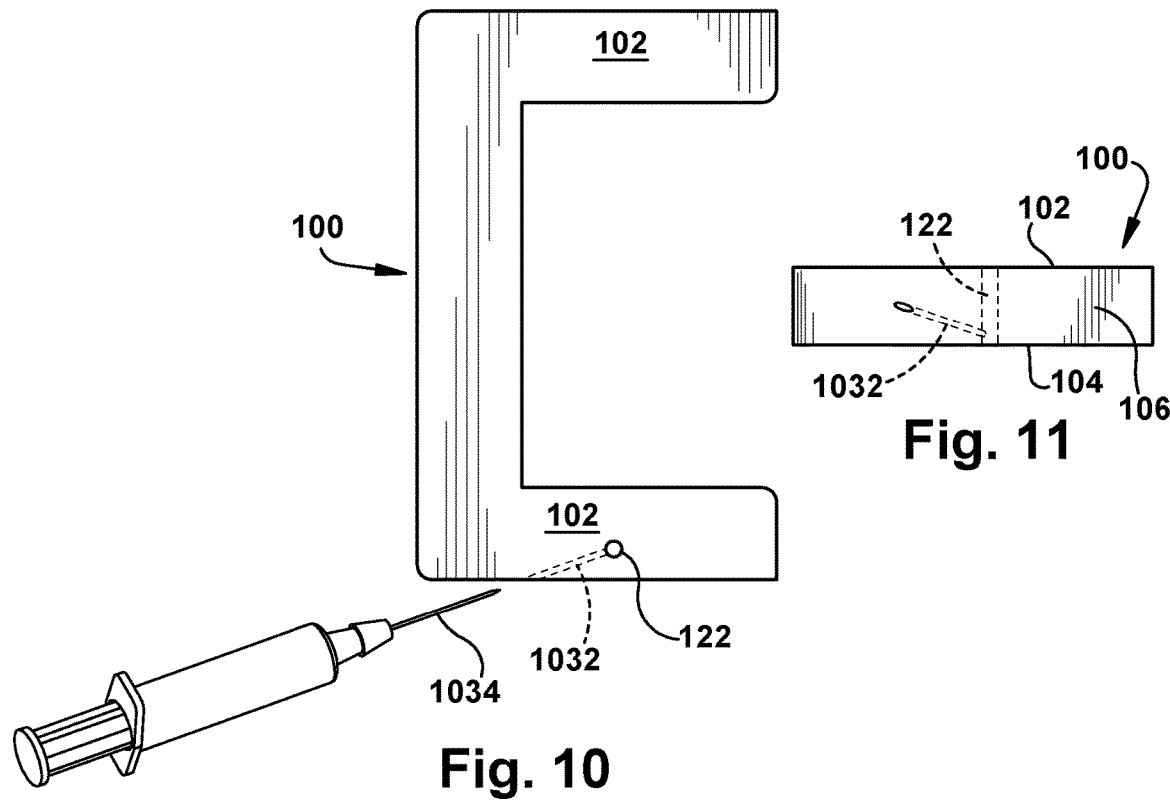
Fig. 10
Fig. 11

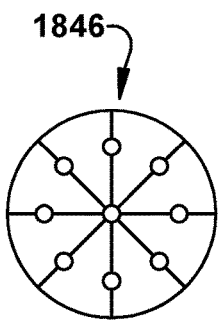
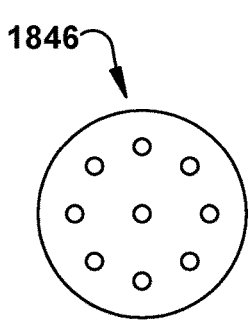
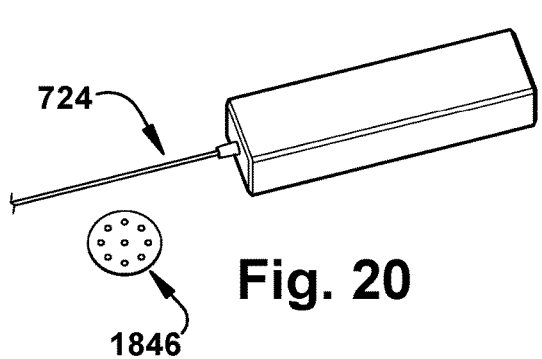
Fig. 18   Fig. 19   Fig. 20
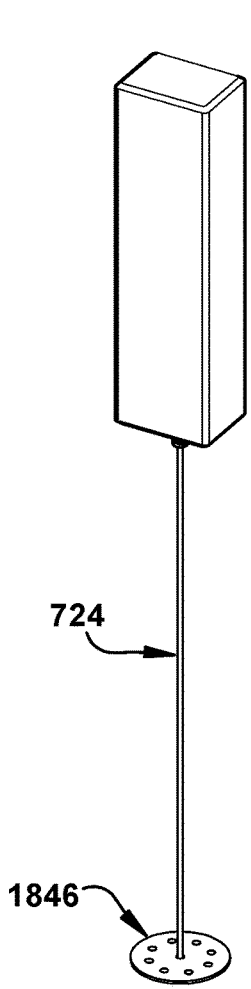
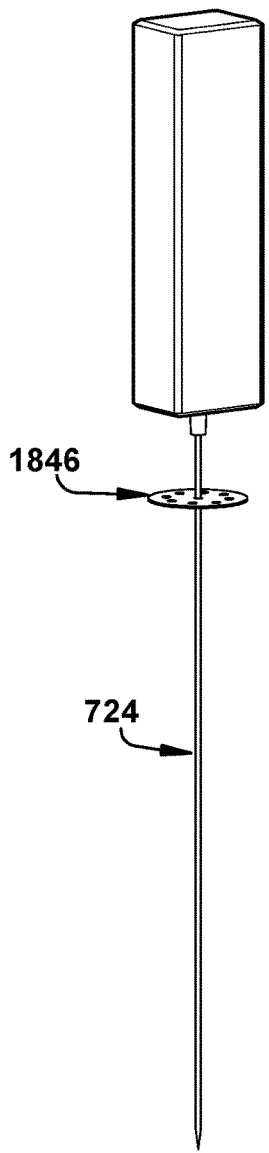
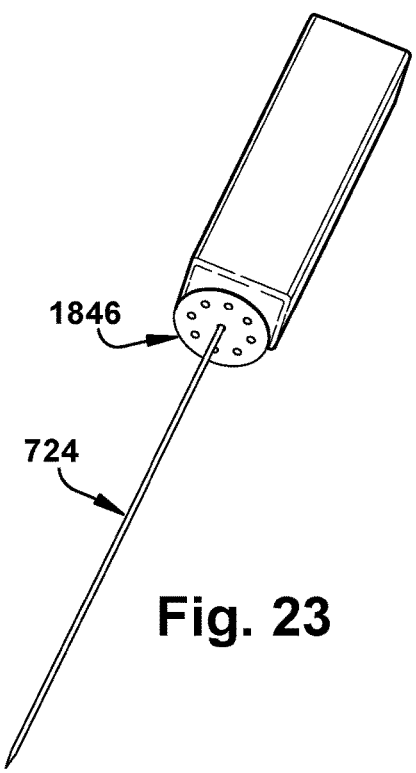
Fig. 21   Fig. 22   Fig. 23

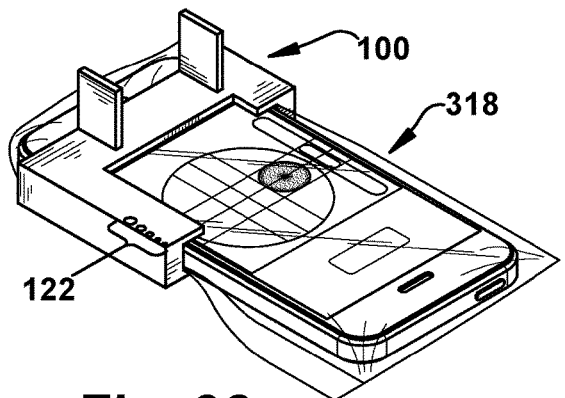
Fig. 30
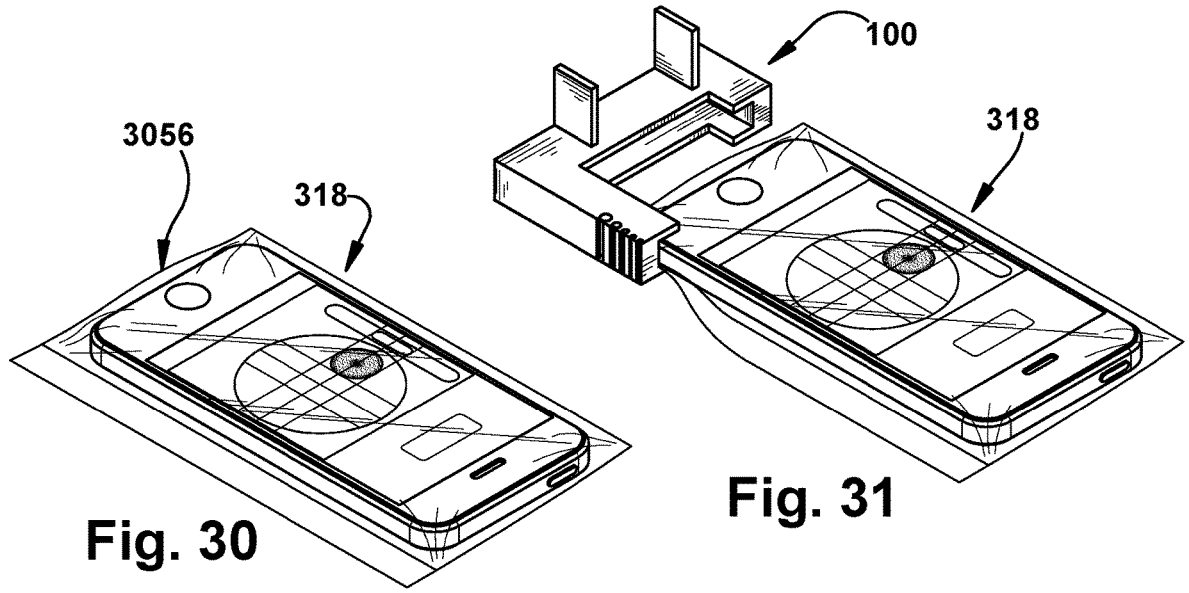
Fig. 31
Fig. 32
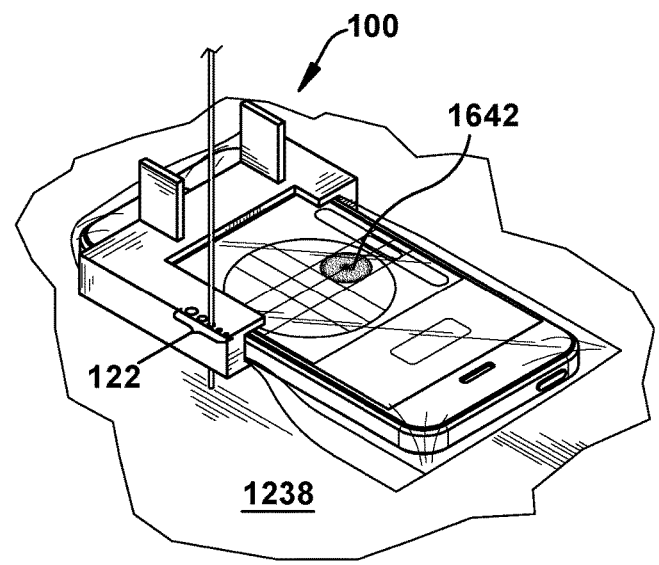
Fig. 33

APPARATUS AND METHOD FOR USE OF AN INCLINOMETER-AIDED NEEDLE GUIDE

RELATED APPLICATION

This application is a divisional of U.S. patent application Ser. No. 15/967,358, filed 30 Apr. 2018, which claims priority from U.S. Provisional Application No. 62/492,628, filed 5 Jan. 2017, the subject matter of both of which is incorporated herein by reference in its entirety.

TECHNICAL FIELD

This disclosure relates to an apparatus and method for use of an inclinometer-aided needle guide and, more specifically, to a smartphone attachment and corresponding software to assist a medical professional with guiding a needle into a patient's body along a predetermined trajectory.

BACKGROUND

Cross-sectional imaging for guiding percutaneous procedures in the human body is known. Such procedures, which may include Computed Tomography (CT), Magnetic Resonance Imaging (MRI), Ultrasound, any other suitable imaging technique(s), or any combination thereof, use direct visualization to determine a safe needle path that hopefully avoids arteries, veins, nerves, bowel, etc. These known procedures include a planning phase in which scout images are obtained to identify a target such as a lesion. Next, as part of the planning phase, a safe path to the lesion is determined including identification of a skin entrance site. The length of the needle required to reach the target along the selected path is determined. After this planning phase, the procedure is carried out. As part of the procedure, the needle is inserted into the skin at an approximate angle determined during the planning phase but only to a minimal or shallow depth. The patient is then moved into an examination gantry of an imaging device such as CT scanner. While in the scanner, images are obtained that identify the actual position of the needle relative to the target and the planned path. The patient is then pulled out from the scanner and the needle is repositioned and inserted deeper. This process is repeated until the target is reached.

SUMMARY

In an aspect, a system for guiding a needle into a target location of a patient's body is provided. The system includes a planned needle guide trajectory and a guide for removable attachment to a smartphone. The guide includes at least one needle guiding aperture extending substantially perpendicularly to a screen of the smartphone. The needle guiding aperture defines an actual needle guide trajectory. An inclinometer application is running on the smartphone. The inclinometer application indicates to a user conformance of the actual needle guide trajectory to the planned needle guide trajectory.

In an aspect, an apparatus for assisting an inclinometer in guiding a needle into a target location of a patient's body is provided. The apparatus includes a top guide surface and a bottom guide surface, longitudinally spaced from the top guide surface by a guide body. An inclinometer-accepting slot extends laterally into the guide body and is longitudinally spaced from both the top and bottom guide surfaces. At least one handle extends longitudinally upward from the top guide surface. At least one needle guiding aperture extends through the guide body substantially perpendicularly to the top and bottom guide surfaces and selectively accepts at least a portion of the needle longitudinally therethrough.

In an aspect, a method for guiding a needle into a target location of a patient's body is provided. A planned needle guide trajectory is provided. An inclinometer with a removably attached guide is provided. The guide includes at least one needle guiding aperture extending substantially perpendicularly to a display of the inclinometer. With the needle guiding aperture, an actual needle guide trajectory is defined. A needle is inserted at least partially into the needle guiding aperture substantially parallel to the actual needle guide trajectory. The inclinometer is maintained in a predetermined orientation with respect to the patient's body. The predetermined orientation is responsive to the planned needle guide trajectory. With the inclinometer maintained in the predetermined orientation with respect to the patient's body, the needle is advanced at least partially through the needle guiding aperture and into the patient's body. With the inclinometer, the actual needle guide trajectory is monitored during advancement of the needle. Conformance of the actual needle guide trajectory to the planned needle guide trajectory is indicated to a user.

BRIEF DESCRIPTION OF THE DRAWINGS

For a better understanding, reference may be made to the accompanying drawings, in which:
FIG. 1 is a perspective top view of an aspect of the present invention;
FIG. 2 is a side view of the aspect of FIG. 1;
FIG. 3 is a top view of the aspect of FIG. 1 in an example use environment;
FIG. 9 is a schematic top view of the aspect of FIG. 1 including an alternate detail configuration;
FIG. 10 is a schematic top view of the aspect of FIG. 1 in an example configuration;
FIG. 11 is a schematic side view of the aspect of FIG. 9;
FIGS. 18-19 are top views of alternate configurations of an accessory item for the aspect of FIG. 1;
FIGS. 20-24 depict a portion of an example sequence of use of the aspect of FIG. 1;
FIGS. 30-35 depict an example sequence of use of the aspect of FIG. 1.

DESCRIPTION OF ASPECTS OF THE DISCLOSURE

Figure 4A:
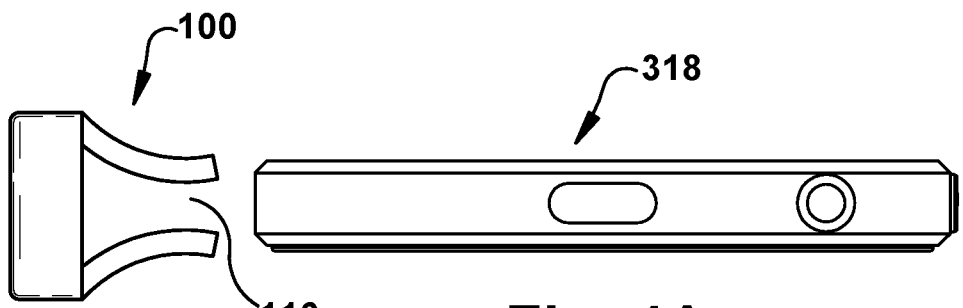
FIG. 4A is an exploded schematic side view of an example configuration of the aspect of FIG. 1.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIG. 1 depicts an apparatus 100 for assisting an inclinometer in guiding a needle into a target location of a patient's body. The apparatus 100 includes a top guide surface 102 and a bottom guide surface 104, longitudinally spaced from the top guide surface 102 by a guide body 106. The "longitudinal" direction, as referenced herein, is substantially parallel to the vertical direction up and down along the page, in the orientation of FIG. 2. An inclinometer-accepting slot 116 extends laterally into the guide body 106 and is longitudinally spaced from both the top and bottom guide surfaces 102 and 104. As referenced herein, the "lateral" plane is orthogonal to the longitudinal direction and is substantially perpendicular to the plane of the page into and out of FIG. 2.

As shown in at least FIGS. 1-3, the guide body 106 may include a grasping segment 108 having laterally spaced first and second grasping segment ends 110 and 112. The grasping segment 108 may be longitudinally bounded by the top and bottom guide surfaces 102 and 104. A side arm 114 may extend orthogonally and laterally from a selected one of the first and second grasping segment ends 110 and 112. The side arm 114 may be a first side arm 114a. The guide body 106 may include a second side arm 114b extending orthogonally and laterally from an other one of the first and second grasping segment ends 110 and 112. When present, the first and second side arms 114a and 114b may both extend in the same direction from the grasping segment 108, such as to form the "C" shaped construct shown in the Figures. The first and second side arms 114a and 114b, when provided, may each be of any desired dimensions and relative lengths for a particular use environment of the present invention. It is contemplated, though, that the first and second side arms 114a and 114b may be configured to assist with holding a particular type of inclinometer. A range of apparatuses 100, each configured to "match" or be used with a particular inclinometer model (such as, but not limited to, including specifically configured first and second side arms 114a and 114b), may be provided.

The inclinometer 318 shown in the Figures for the sake of description is a smartphone running an inclinometer software application. However, it is contemplated that any suitable digital and/or analog inclinometer, such as, but not limited to, a bubble level or a single-function electronic inclinometer, may be used with an appropriately configured apparatus 100.

The inclinometer-accepting slot 116 may be configured to concurrently lie adjacent to and/or contact at least three adjoining orthogonal sides of the inclinometer 318, as shown in the example use view of FIG. 3. The inclinometer-accepting slot 116 may extend completely laterally through the guide body 106, such that the apparatus 100 slides entirely onto and around the inclinometer 318, or may instead be a "blind" aperture which limits the extent to which the inclinometer 318 can be inserted into the apparatus 100.

Figure 4B:
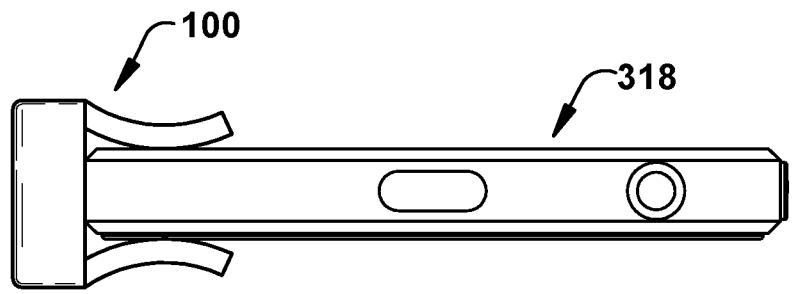
FIG. 4B is an assembled view corresponding to FIG. 4A.
Figure 5A:
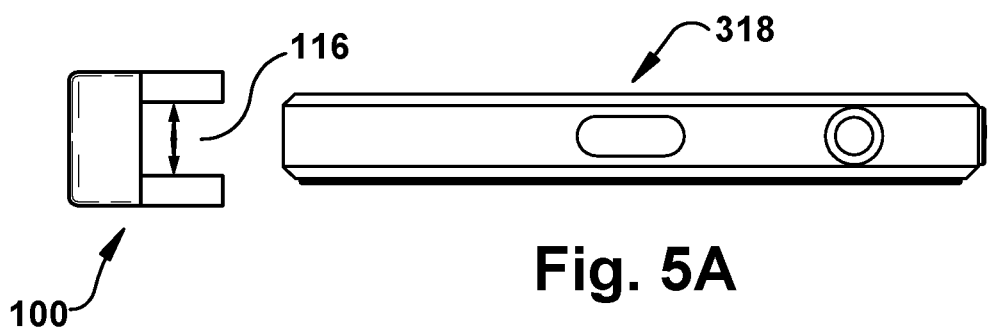
FIG. 5A is an exploded schematic side view of an example configuration of the aspect of FIG. 1.
Figure 5B:
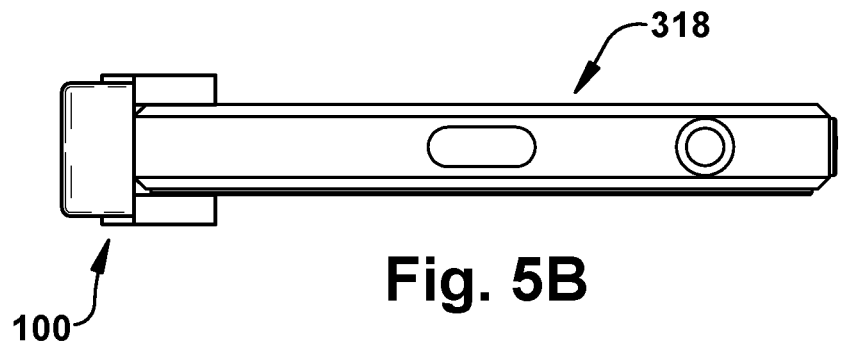
FIG. 5B is an assembled view corresponding to FIG. 5A.

A simple inclinometer-accepting slot 116, such as the rectangular slot of FIGS. 1-3 could be sized to slide relatively smoothly with respect to the inclinometer 318, or could hold the inclinometer 318 in a frictional or interference fit. As shown in the example of FIGS. 4A-4B, the guide body 106 could include an at least partially "spring clip" type inclinometer-accepting slot 116, which "clips" or "clamps" onto at least a portion of the inclinometer 318 under elastic deformation. Another example inclinometer-accepting slot 116 is shown in FIGS. 5A-5B and includes a "vice-type" structure which has a longitudinally varying opening and a mechanism which allows the jaws thereof to move into "open" and "closed" positions (e.g., via a rack-and-pinion structure or in any other manner) to "bite" down on the inclinometer 318 in lieu of the lateral sliding motion used in the other inclinometer-accepting slots 116 shown herein. However, one of ordinary skill in the art will be able to associate the apparatus 100 with an inclinometer 318 as desired, with any desired amount (or none) of "gripping" of the inclinometer 318, for a particular use environment of the present invention.

With reference back to FIG. 1, at least one handle 120 (two shown) may extend longitudinally upward from the top guide surface 102. The handle(s) 120 may have any desired configuration, including, but not limited to, the depicted simple rectangular "fin" type, an ergonomically curved construct, or any other desired type of handle 120 operative to assist a user with holding the apparatus 100. During operation of the apparatus 100, the user can hold the handles 120 in the "pincher" type grip shown in FIG. 3. The handles 120 may assist with achieving desired control over motion of the apparatus 100, particularly when an inclinometer 318 is being supported or held by the apparatus 100.

At least one needle guiding aperture 122 may extend through the guide body 106 substantially perpendicularly to the top and bottom guide surfaces 102 and 104, as shown in at least FIG. 1. The needle guiding aperture 122 may selectively accept at least a portion of the needle longitudinally therethrough, as will be discussed further below. The at least one needle guiding aperture 122 may extend through a portion of the guide body 106 forming a side arm 114, for example, particularly if such might be helpful in avoiding unwanted contact between the needle and the inclinometer 318.

As shown in FIG. 1, the at least one needle guiding aperture 122 may be one of a plurality of needle guiding apertures 122. Each needle guiding aperture 122 may have a different largest cross-sectional dimension (e.g., a diameter when the needle guiding aperture 122 is a round hole), measured laterally, than the other needle guiding apertures 122. Each needle guiding aperture 122 may also or instead have any other physical difference from at least one other needle guiding aperture 122, other than its position on the apparatus 100. As a result, a plurality of needle guiding apertures 122 can be provided, with each one suited for a different guiding task (e.g., for guiding a different size needle).

Figure 6:
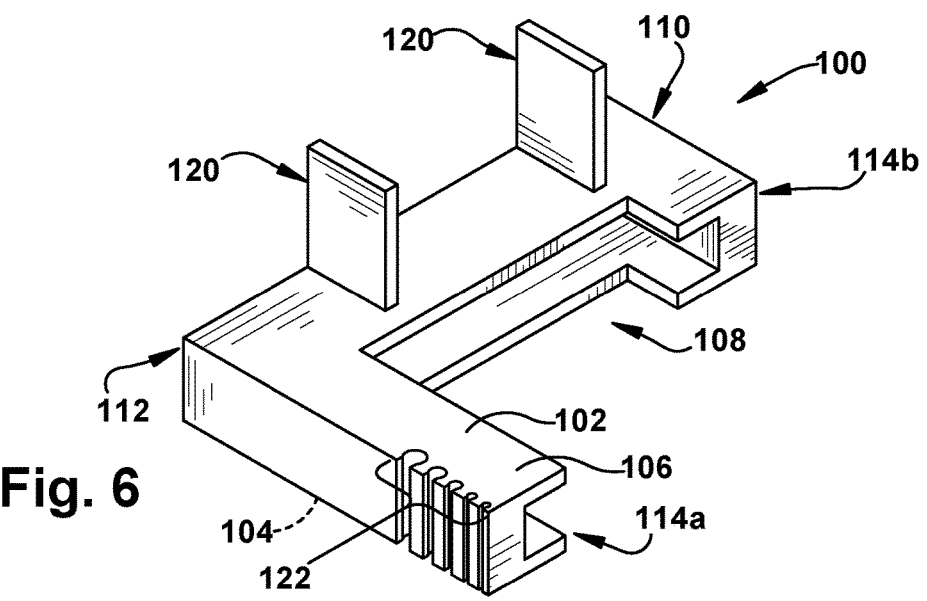
FIG. 6 is a perspective top view of the aspect of FIG. 1 having an alternate detail configuration.
Figure 7:
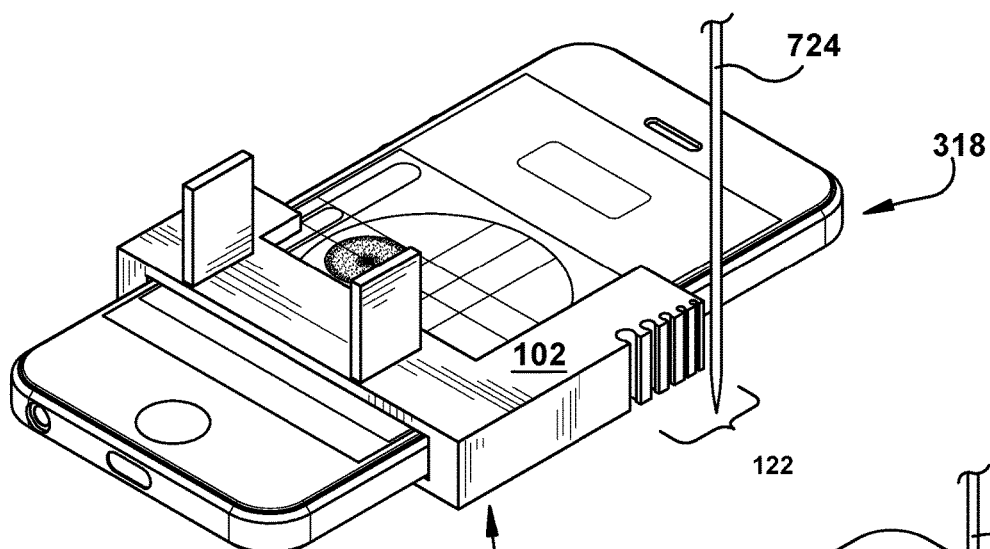
FIGS. 7-8 depict an example sequence of use of the aspect of FIG. 5.
Figure 8:
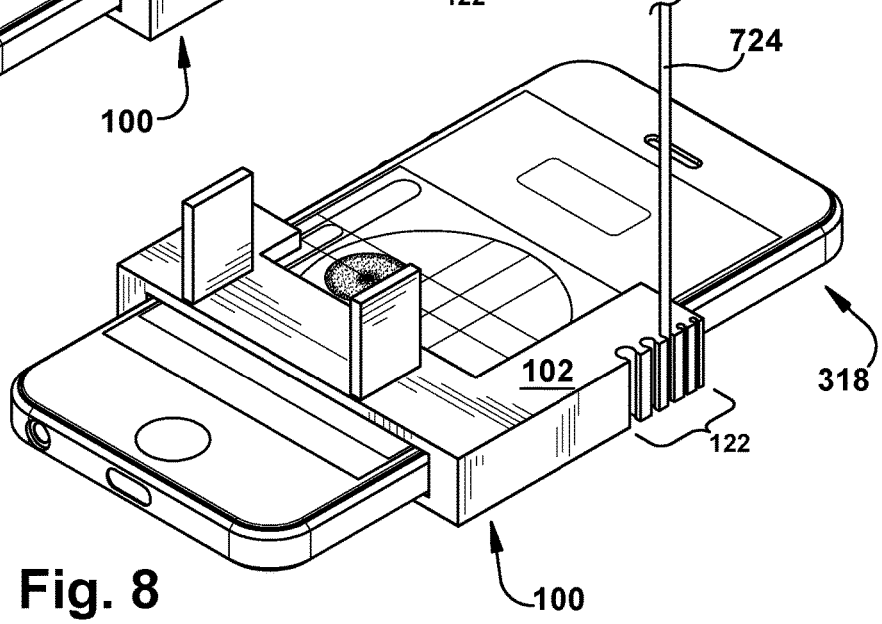

As shown in FIGS. 6-8, the at least one needle guiding aperture 122 may be a longitudinally extending slot, providing laterally oriented access for the needle thereinto. For example, and as shown in FIGS. 7-8, a needle 724 could be placed laterally beside the apparatus 100, and then the needle 724 and apparatus 100 could be moved laterally relative to one another until the needle 724 extends substantially longitudinally between the top and bottom guide surfaces 102 through the slot-type needle guiding aperture 122, as shown in FIGS. 6-8. This slot-type needle guiding aperture 122 may be helpful when longitudinal movement of the needle 724 is constrained, such as, for example, if a lower end of the needle 724 is already penetrating into the patient's tissue below the apparatus 100. For the sake of determination of the "largest cross-sectional dimension" for a slot-type needle guiding aperture 122, the open side or "mouth" of the slot (through which the needle 724 enters) could be considered to be bounded by a plane substantially parallel to the local longitudinally extending portion of the guide body 106 adjacent to the "mouth" of the slot.

FIG. 9 schematically illustrates another example option of a configuration of a needle guiding aperture 122, wherein a jaw portion 926 moves relative to the guide body 106, such as in the substantially parallel motion provided by the guide tracks 928 attaching the jaw portion 926 to the guide body 106. In the configuration shown in FIG. 9, the needle guiding aperture 122 comprises a pair of notches 930 in the jaw portion 926 and guide body 106. These notches 930 move laterally with respect to each other, via relative lateral motion of the jaw portion 926 and the guide body 106 to accommodate any of a variety of needle 724 sizes.

With reference now to FIGS. 10-11, an anesthesia port 1032 may extend obliquely through a portion of the guide body 106 and be in fluid communication with the at least one needle guiding aperture 122 at the bottom guide surface 104. Through use of the anesthesia port 1032, an anesthetic syringe 1034 could penetrate into the guide body 106 and be used to inject a local anesthetic into the patient tissue at or near an intersection of the needle guiding aperture 122 with the patient tissue—i.e., the location where the needle 724 will be penetrating into the patient tissue under guidance from the apparatus 100.

Figure 12:
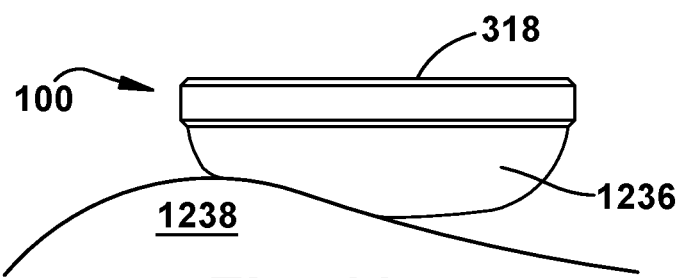
FIGS. 12-14 are schematic side views of example configurations of the aspect of FIG. 1.
Figure 13:
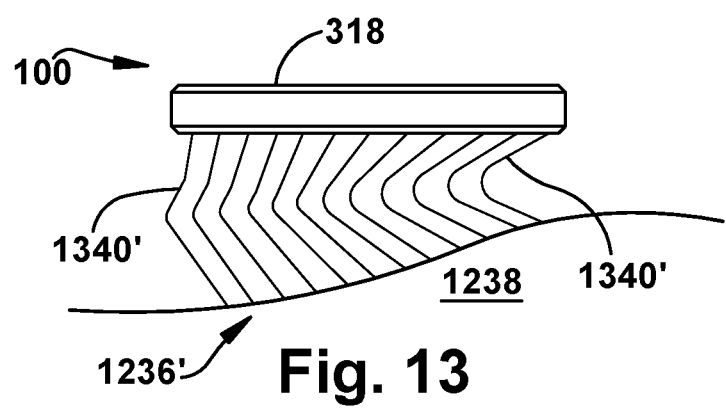
Figure 14:
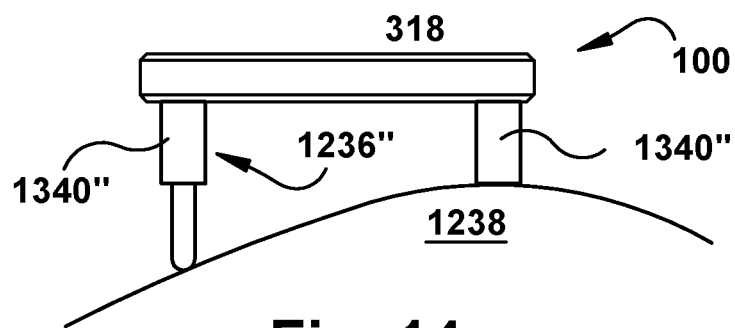

A device leveler 1236 may extend longitudinally downward from the guide body 106, below the bottom guide surface 104. When present, the device leveler 1236 may be used to help maintain a desired orientation of the inclinometer 318 in space relative to the patient tissue 1238, regardless of the local contours of that patient tissue 1238. The device leveler 1236, when present, may have any suitable form. For example, a malleable "beanbag" type device leveler 1236 is shown in FIG. 12, with the device leveler 1236 including a gel pad or other structure which facilitates contact between a relatively large, varying-profile surface of the device leveler 1236 and the patient tissue 1238. Another example device leveler 1236' is shown in FIG. 13. Here, instead of the somewhat planar, surface contact shown in FIG. 12, a plurality of bendable or malleable device legs 1340' each makes point contact with the patient tissue 1238. The device legs 1340' can be bent by the user as desired to help achieve and maintain a desired "leveling", or other orientation of the inclinometer 318 with respect patient service 1238. Like the device leveler 1236' of FIG. 13, the device leveler 1236" of FIG. 14 includes a plurality of device legs 1340" which each makes point contact with the patient tissue 1238. However, the device legs 1340" of FIG. 15 each include a telescoping configuration, to allow for the longitudinal dimension of each device leg 1340" to be changed and then maintained at a desired length (optionally with the aid of a set screw or frictional fit within the telescoping). Regardless of the nature of any device leveler 1236 provided (whether depicted or not herein), one of ordinary skill in the art can achieve a desired orientation of the inclinometer 318 with respect to the patient tissue 1238 with a device leveler 1236 configured for particular use environment.

Figure 15:
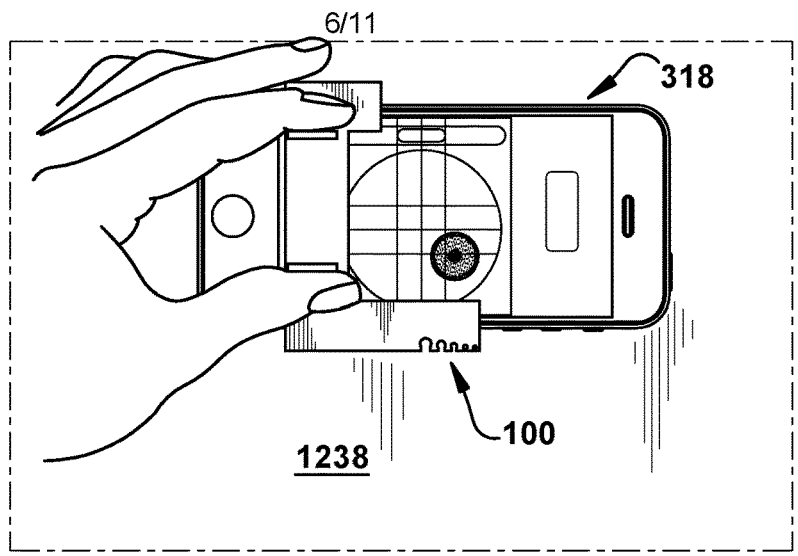
FIGS. 15-17 depict a portion of an example sequence of use of the aspect of FIG. 1.
Figure 16:
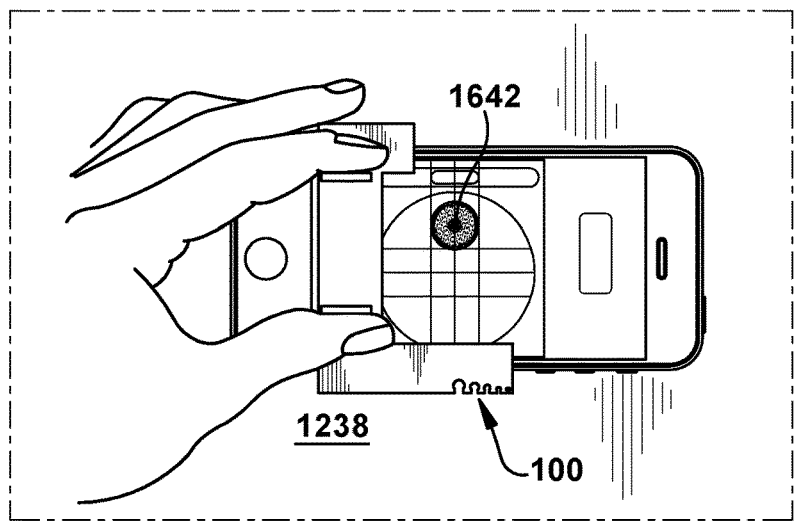
Figure 17:
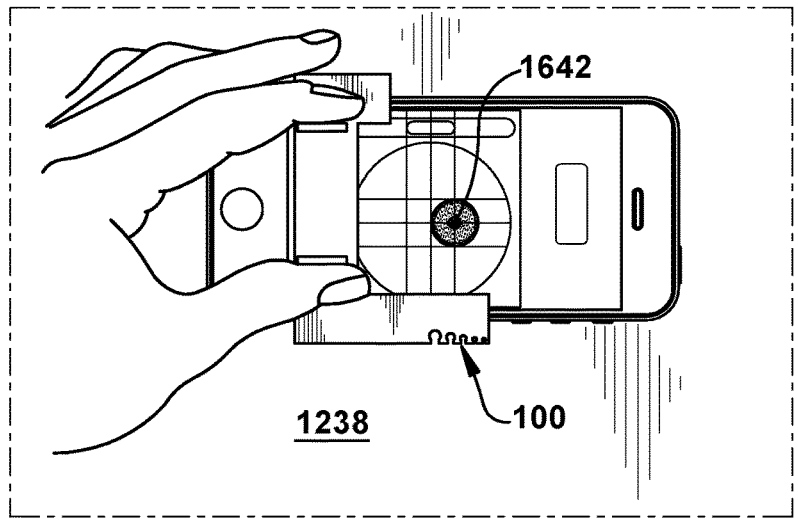

The sequence of FIGS. 15-17 show how a user can move the apparatus 100, with an associated inclinometer 318, to achieve a desired trajectory of the needle guiding aperture 122 of the apparatus 100 with respect to an underlying patient tissue 1238 surface. In FIG. 15, the inclinometer 318 is associated with the apparatus 100 and the user grasps the handles 120 to at least partially lift the inclinometer 318 from the patient tissue 1238. As shown in FIG. 16, a target indicator 1642 of the inclinometer 318 is shown as being off-center from a desired target location. Here the target indicator 1642 is a red dot and the desired target location is represented by the center of a "crosshairs" graphic. The desired target location is graphically depicted by the inclinometer 318 (which may comprise a smartphone) responsive to the "knowledge" by the inclinometer 318 of the planned trajectory of the needle guiding aperture 122 of the apparatus 100. That planned needle guide trajectory is stored in a computer-readable media readable by the inclinometer/smartphone. When the target indicator 1642 is "on target" to the crosshairs, the needle guiding aperture 122 can be considered to have achieved a desired trajectory with respect to an underlying patient tissue 1238 (i.e., the planned needle guide trajectory). However, it is contemplated that any desired technique may be used to indicate to a user whether the needle guiding aperture 122 is in position as desired, and/or a direction, magnitude, or any other property of motion which would be appropriate to move the needle guiding aperture 122 toward the predetermined desired trajectory, as discussed further below. The target indicator 1642 can include, or be a part of, any desired user-perceptible indicating scheme, such as, but not limited to, an audible signal, a numerical signal, a graphical representation of one or more arrows, a graphical representation of a bull's-eye or crosshairs, any other graphical signal or representation, a haptic indication, or any other desired user-perceptible indicator or combination thereof.

The user then can manipulate the apparatus 100, with the associated inclinometer 318, as shown in FIG. 17 to "shift" the target indicator 1642 toward a desired position. For example, as shown in FIG. 17, the apparatus 100 has been manipulated to move the target indicator 1642 substantially into the vertical center of the screen (in the orientation of FIG. 17), but further motion would be appropriate to shift the target indicator 1642 toward the horizontal center of the screen (in the orientation of FIG. 17). Thus, the apparatus 100 and inclinometer 318 can be used in almost a "joystick" type manner to shift or precess the trajectory of the needle guiding aperture 122 with respect to an underlying patient tissue 1238 surface, at a known desired needle 724 site on the patient tissue 1238 surface.

With reference now to FIGS. 18-24, the inclinometer 318 may include an optical sensor 2444, such as a camera when the inclinometer 318 is associated with a smart phone, as in the Figures. The apparatus 100 will then include, and/or be used with, a contrast indicator 1846 for selective engagement with the needle 724. The contrast indicator 1846 may be detectable with the optical sensor 2444 for assisting with guiding the needle 724 into the target location on the patient tissue 1238, and at a desired trajectory and insertion depth. FIGS. 18-19 depict two different example configurations of a suitable contrast indicator 1846. Also contemplated, though not shown in FIGS. 18-19, is a "bead" or spherical contrast indicator. The sequence of FIGS. 20-23 show the contrast indicator 1846 being placed on 2007 24, and slid up the needle 724, with the "indicating" side of the contrast indicator 1846 (i.e., a surface including some sort of indicia perceptible by the optical sensor 2444) facing downward, toward the inclinometer 318.

Figure 24:
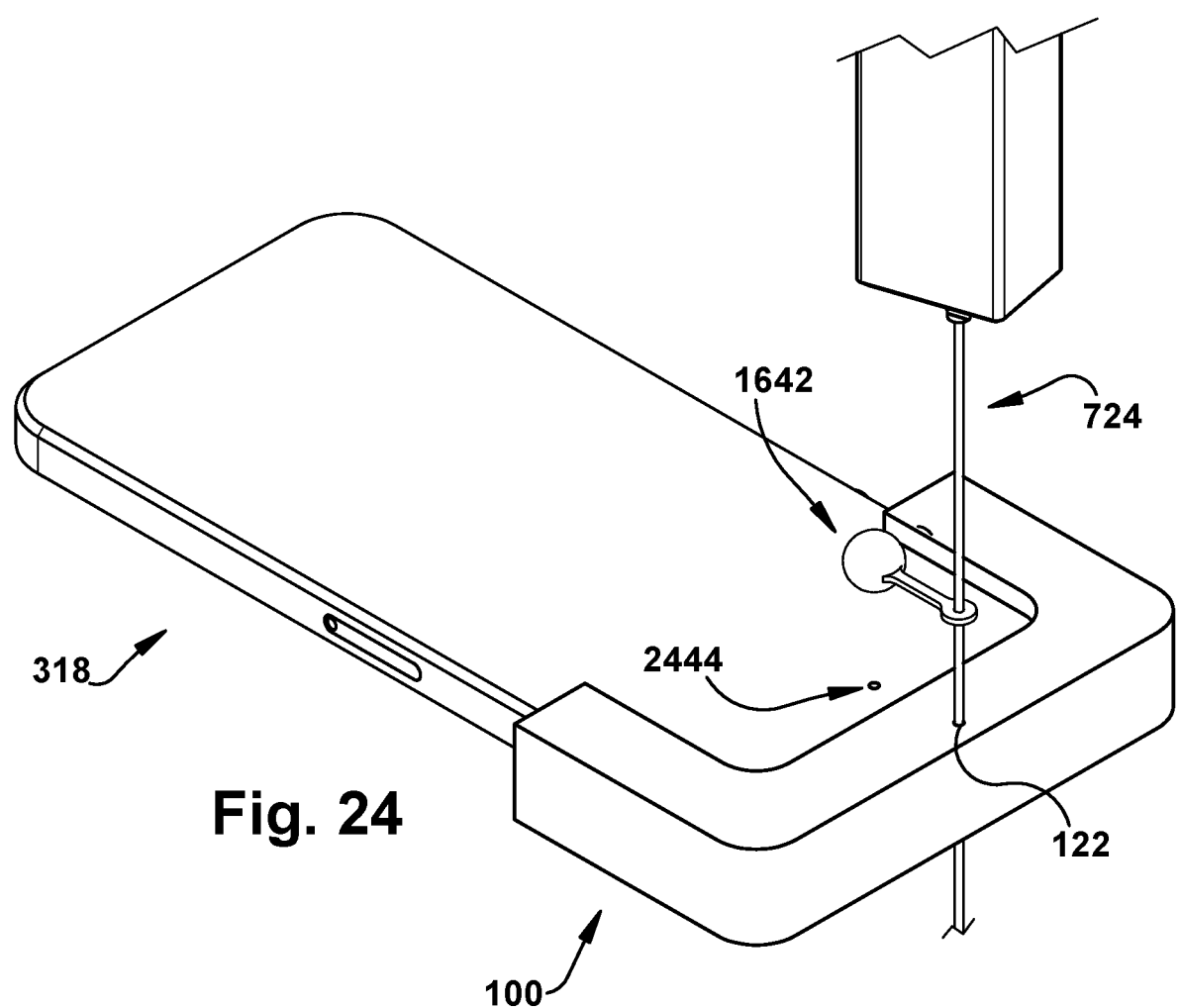

FIG. 24 depicts how the optical sensor 2444 can be used to calculate distance traveled by the needle 724 using the apparent size of the contrast indicator 1846, with specific use of the formula slope $(m)=(y2-y1)/(x2-x1)$. (The apparatus 100 shown in FIG. 24 differs slightly in configuration from other apparatuses 100 shown graphically, in order to simplify the below discussion, but one of ordinary skill in the art can readily configure a suitable apparatus 100 for a particular use environment.) In this case, relating an apparent change in diameter of the bead-type contrast indicator 1846 between a first insertion position x1 and a second, deeper/later insertion position x2 will help the user and/or the inclinometer 318 calculate the change in needle distance traveled between those two positions (y2-y1). A calibration procedure of any desired type may occur, such as, but not limited to, measurement of the change of apparent contrast indicator 1846 size due to needle 724 travel over a known longitudinal distance relative to the optical sensor 2444. The contrast indicator 1846 (and its change in apparent size) could be displayed to the user, in some use environments of the apparatus 100.

In order to use this formula, the apparent size of the contrast indicator 1846 can be determined using the camera and image processing to determine the maximum dimension (e.g., diameter) of at least a portion of the contrast indicator 1846 as measured in pixels, given a known insertion depth (e.g., an insertion depth of zero, with the distalmost end of the needle 724 just touching the patient tissue 1238 surface). The position of the contrast indictor 1846 with respect to the optical sensor 2444 is also known, by virtue of its attachment to the needle 724.

The contrast indicator 1846 can then be moved to a point closer to the optical sensor 2444 via insertion of the needle 724 into the patient tissue 1238. The contrast indicator 1846 size in terms of pixels as above is measured.

The change in distance of the contrast indicator 1846 from the optical sensor 2444=(y2−y1)

The change in contrast indicator 1846 size in pixels=(x2−x1)

The linear equation describing this relationship is $\Delta y = m \Delta x$

This formula can be used in practice by setting the needle 724 insertion depth to zero, or any other desired initial value, by setting a "tare" on the inclinometer software application or in any other desired manner. The pixel size of the contrast indicator 1846 is noted at this "zeroed" position. As the needle 724 is inserted into the patient tissue 1238 and the contrast indicator 1846 comes closer to the optical sensor 2444, the application continuously determines the size of the contrast indicator 1846 in terms of pixels (image processing), compares it to the original zero position contrast indicator 1846 size to determine $\Delta x$ (in a continuous or step-measure-step type manner) and from these values calculates the change in needle 724 insertion depth/distance $\Delta y$. $\Delta y$ is then displayed on the screen as desired to provide feedback to the user on the needle 724 insertion distance. There could also be visual, audible, haptic, and/or any other user-perceptible feedback when the needle 724 is closely approaching, or has reached, a predetermined depth of insertion.

Figure 25:
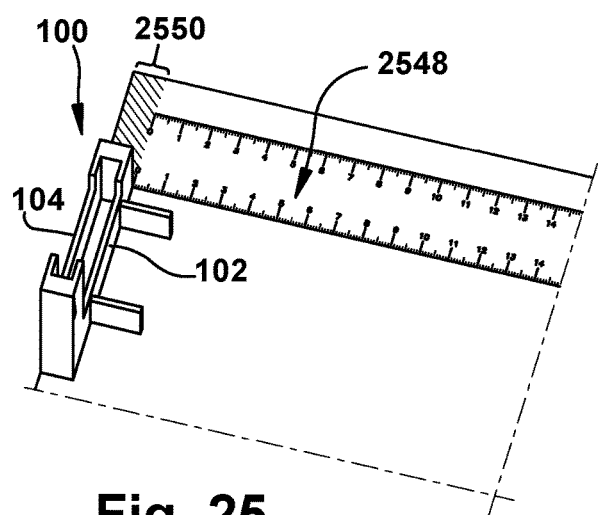
FIGS. 25-29 depict a portion of an example sequence of use of the aspect of FIG. 1.
Figure 26:
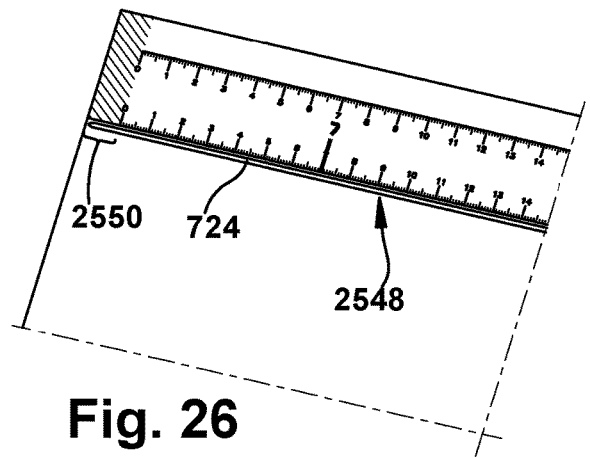
Figure 27:
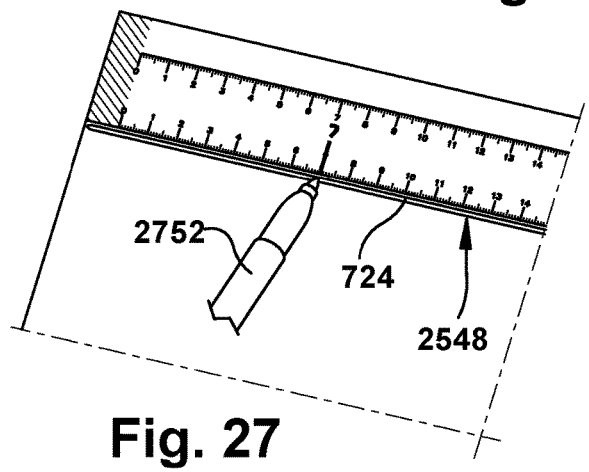

FIGS. 25-29 depict a manner in which a depth of needle 724 insertion into the patient tissue 1238 can be indicated and/or controlled. FIGS. 25-27 show a scale or ruler 2548 which can be used to help prepare a needle 724 for a depth-controlled and/or depth-monitored insertion into the patient tissue 1238. In FIG. 25, the apparatus 100 is being compared against the ruler 2548 so that the thickness of the apparatus 100, between the top and bottom guide surfaces 102 and 104, can be taken into account during needle depth measurements. A "tare zone" 2550 is then blocked off, and the ruler 2548 is shifted over (here, toward the right of FIG. 25) so that the insertion depth is not undesirably offset by the thickness of the guide body 106. In FIG. 26, the needle 724 is placed into alignment with the ruler, with a distal tip of the needle extending across the tare zone 2550 so that the origin of the ruler 2548 is displaced from the distalmost end of the needle 724 by the thickness of the guide body 106. The user then locates, on the ruler 2548, a desired insertion depth for the needle 724 into the patient tissue 1238. In the example of these Figures, an insertion depth of 7 cm is indicated.

With reference now to FIG. 27, a marking device 2752 is used to two- and/or three-dimensionally alter the needle 724 at the desired insertion depth as indicated on the ruler 2548. (Again, this insertion depth is offset from the distalmost end of the needle 724 but thickness of the guide body 106, so the alteration or marking will actually occur slightly more than 7 cm from the distalmost end of the needle 724, in this example.) Any desired user-perceptible marking scheme could be provided, such as, but not limited to, an ink marking on the needle body, a crimped collar 2854 around the needle body, any other desired marking technique, or any other combination thereof.

Figure 28:
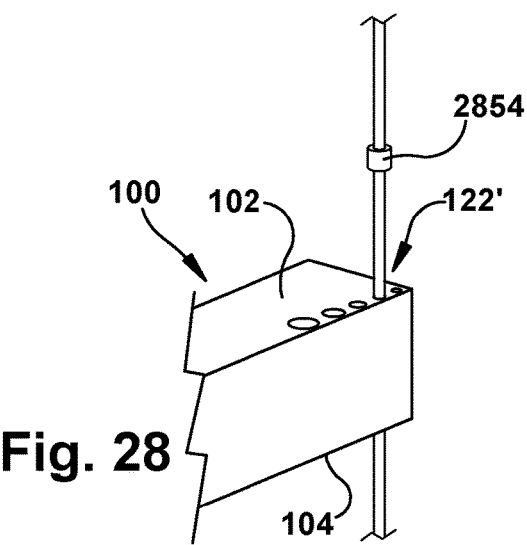
Figure 29:
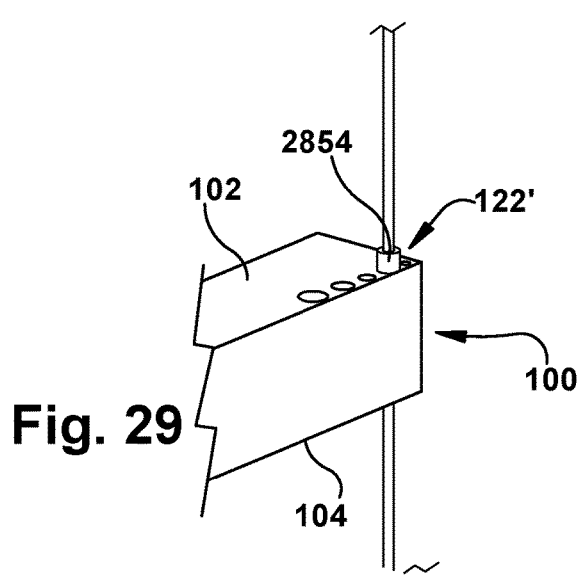

In FIG. 28, the needle 724 has been inserted into the needle guiding aperture 122, and the needle 724 is being moved downward, into the underlying patient tissue 1238 surface. In FIG. 29, the crimped collar 2854 has come into contact with the top guide surface 102. Here, since the crimped collar 2854 has a larger diameter than the needle guiding aperture 122, the crimped collar 2854 will help to prevent further insertion of the needle 724 once the desired insertion depth has been achieved. It is contemplated, however, that even a two-dimensional marking (e.g., an ink or paint mark) can assist a user with avoiding overinsertion of the needle 724 into the patient tissue 1238.

FIGS. 30-35 depict a method for guiding a needle 724 into a target location of a patient's body, using a system including an apparatus 100 as described above.

The system as shown and described herein includes a planned needle guide trajectory. That is, the user, as a starting point, has information pertaining to an insertion location for the needle 724 into the patient tissue 1238, as well as a desired planned needle guide trajectory to take the needle 724 from that insertion location to a desired target site within the patient tissue 1238 (e.g., to a subcutaneous cyst, seed insertion site, biopsy location, or for any other desired subcutaneous needle-assisted task or combination thereof). The user will also know a desired insertion depth for the needle 724 at that insertion location and along that planned needle guide trajectory. This information can come from any suitable source, including, but not limited to, preoperative imaging of the patient tissue 1238 and can be stored in a computer-readable media readable by the smartphone 318 or other electronic inclinometer, for retrieval and comparison as disclosed herein. One of ordinary skill in the art can readily generate such "orientation" or "targeting" information for a particular use environment.

The apparatus 100 as shown in FIGS. 30-35 is a guide 100 for removable attachment to a smartphone, such as a smart phone 318 running an inclinometer software application, as depicted. The guide 100 includes at least one needle guiding aperture 122 extending substantially perpendicularly to a screen of the smartphone 318. The needle guiding aperture 122 defines an actual needle guide trajectory—i.e., a line along which the needle 724 is actually extending when inserted into the needle guiding aperture 122. It is contemplated that a plurality of needle guiding apertures 122 may be provided on a single guide 100, and one of ordinary skill in the art can then choose, potentially with the assistance of a surgical guide (e.g., planning software), the specific needle guiding aperture 122 into which the needle 724 is to be inserted. For example, the user can select the smallest needle guiding aperture 122 within which the needle 724 can still move freely longitudinally.

As previously mentioned, an inclinometer application may be running on the smartphone 318 acting as inclinometer. The inclinometer application (on the smartphone) can indicate to a user conformance of the actual needle guide trajectory to the planned needle guide trajectory as stored in the computer-readable media readable by the smartphone 318.

Because the user knows the actual needle guide trajectory, the planned needle guide trajectory, and the desired insertion location, the apparatus 100 can be used to help guide the needle 724 into a desired depth, trajectory, and location of insertion into the patient tissue 1238, toward a desired target site. The planned needle guide trajectory could be relative to a local (e.g., on the patient, such as with reference to a known patient marker device) and/or global (e.g., with respect to the operating room as a whole and/or to the Earth) frame of reference. The below description presumes that the inclinometer measures the actual needle guide trajectory with respect to the Earth, such as by using accelerometers provided in the smartphone 318.

In FIG. 30, a sterile cover 3056 may be provided for selective engagement with the smartphone 318 to fully enclose the smartphone 318 and become interposed between the smartphone 318 and the guide 100. In this manner, the smartphone 318 is not required itself to be sterilized for use in the surgical field. Once the sterile cover 3056, when provided, is enclosing the smartphone 318 as desired, the guide 100 can be removably attached to the smartphone 318, as shown in the sequence of FIGS. 31-32. To wit, the inclinometer 318 is inserted into the inclinometer-accepting slot 116, and the apparatus 100 is slid laterally onto the smartphone 318 to any desired position or relationship. It is contemplated that the apparatus 100 could have a physical limit (e.g., a blind-ended inclinometer-accepting slot 116) to assist with achieving a desired relative relationship with the smartphone 318 serving as the inclinometer. It is also contemplated the smartphone 318 could include some sort of physical stop or user-perceptible marking to help the user achieve the desired relationship between the apparatus 100 and the smartphone 318.

Again, as previously noted, the needle guiding aperture 122 (which may extend substantially perpendicularly to a display of the smartphone 318) defines an actual needle guide trajectory. As shown in FIG. 33, a needle 724 is inserted at least partially into a selected needle guiding aperture 122 and thus achieves a position substantially parallel to the actual needle guide trajectory. When the needle guiding aperture 122 is of the "slot" type, the needle 724 may be laterally moved into engagement with a slot-type needle guiding aperture 122. This may be helpful, for example, when the distal most tip of the needle is inserted very slightly into the patient tissue 1238 at the insertion location, in order to "anchor" the needle 724 during movement of the apparatus 100 under guidance from the smartphone 318.

As previously described, the smartphone 318 can be placed into a "coarse" relative position with respect to the patient's body by the user lightly placing the distalmost tip of the needle 724 against the patient tissue 1238 at the desired insertion location, or by a very slight (to avoid potential patient tissue damage) insertion of the needle 724 into the patient tissue 1238. With that tip of the needle 724 held in place against the desired insertion location and with the needle 724 being in engagement with the apparatus 100, the smartphone 318 can be precessed or otherwise moved with respect to the patient tissue 1238. This can be considered to be "fine" relative positioning, and is carried out until the target indicator 1642 indicates that the actual needle guide trajectory is in substantial conformance to the planned needle guide trajectory. At this point, the apparatus 100, and by extension the needle guiding aperture 122 and associated needle 724, can be considered to be "dialed in" at the predetermined orientation with respect to the patient's body, and the needle 724 is "pointing" along the direction and trajectory at which it should be inserted into the patient tissue 1238. The smartphone 318 is then maintained in such a predetermined orientation with respect to the patient's body, with the predetermined orientation being imposed responsive to the planned needle guide trajectory.

Figure 34:
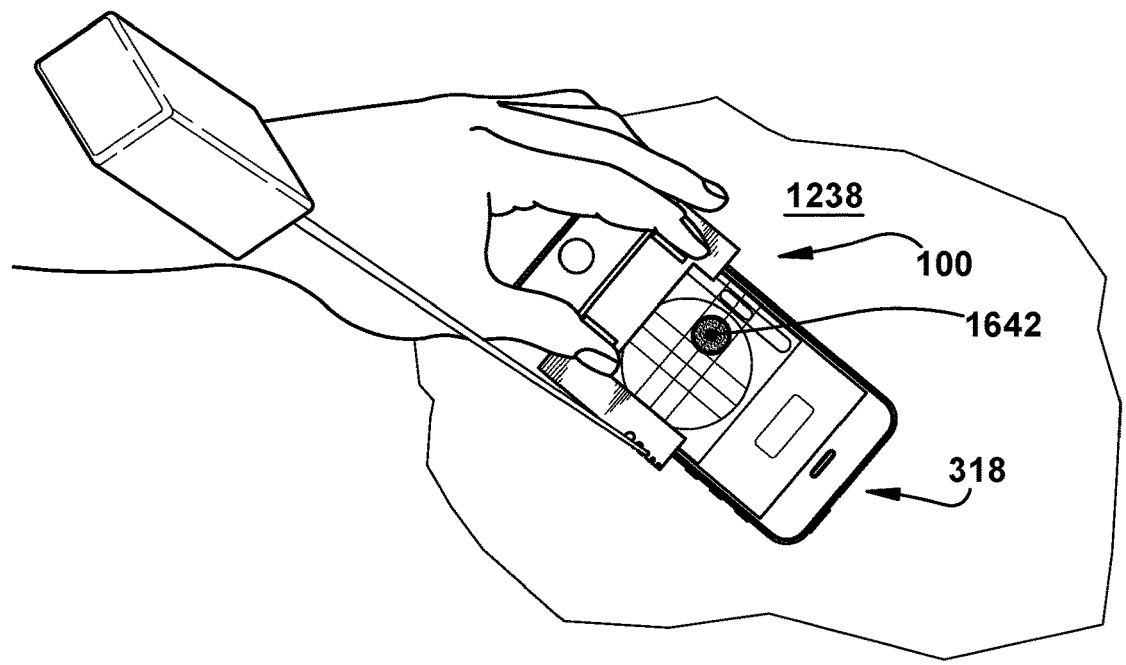

With the smartphone 318 maintained in the predetermined orientation with respect to the patient's body, the needle 724 is advanced at least partially through the needle guiding aperture 122 and into the patient's body, as depicted in FIG. 34. With the smartphone 318, the actual needle guide trajectory is monitored during advancement of the needle 724, and a user receives indication of conformance of the actual needle guide trajectory to the planned needle guide trajectory. It is contemplated that, during advancement of the needle 724, the needle 724 could slightly deviate from the planned needle guide trajectory, and the smart phone 318 may be configured to provide an audible, visual, haptic, or other user-perceptible indication when the needle 724 starts to leave the planned trajectory course.

The system may indicate to a user when the needle 724 has achieved a predetermined insertion depth, through a collar 2854 or other depth of insertion marking, as previously described. A target indicator 1642 could be used in combination with an optical sensor 2444 to assist with conforming the actual needle guide trajectory to the planned needle guide trajectory. Intraoperative imaging could also or instead be present to help the apparatus 100 guide the user to carry out a predetermined insertion procedure.

Figure 35:
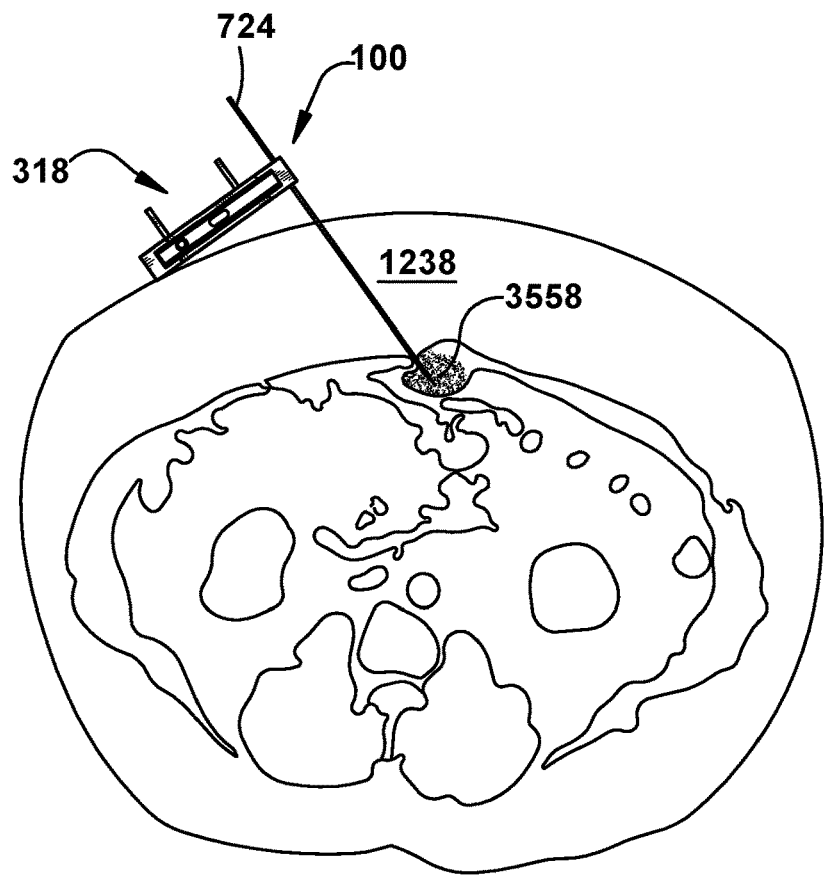

Regardless of the options, configurations, features, operations, and other aspects of the system and apparatus 100 shown and described herein, however, once the needle 724 has been inserted into the patient tissue 1238 at a desired insertion location and along the planned needle guide trajectory, as well as to a desired insertion depth, the distal most tip of the needle should be located at or near a subcutaneous target site 3558 within the patient tissue 1238, as shown schematically in the cross-sectional intraoperative image of FIG. 35.

Once the needle 724 guidance is no longer desired, the user may remove the apparatus 100 from the needle 724 in any desired manner. For example, the apparatus 100 could be longitudinally slid off the proximal end of the needle 724 or, when the needle guiding aperture 122 is of the "slot" type, the apparatus 100 could be moved laterally out of engagement with the needle 724. The needle 724 can be used to accomplish the desired task at the target site 3558, and then the needle 724 can be withdrawn, in any desired manner, from the patient tissue 1238. The apparatus 100 can be removed from the smartphone 318, and any provided sterile cover 3056 could also be disengage from the smartphone 318. The apparatus 100 could be discarded or sterilized for reuse, as desired.

It is contemplated that an inclinometer 318 and apparatus 100 could be provided as a single-piece unit, with the apparatus 100 not intended to be removed from the inclinometer 318 after completion of the manufacturing process, other than as needed for repair or refurbishment. That is, the user will receive, store, operate, clean, and otherwise interact with the inclinometer 318 and apparatus 100 as a single-piece device—the apparatus 100 forming a portion of the housing of the inclinometer 318, effectively.

It is also contemplated that a range of apparatuses 100 could be provided, with each apparatus 100 of the range having different overall dimensions, different configuration and/or dimensions of needle guiding apertures 122, different configurations of handles 120, or any other desired differences, in order to create a "library" of apparatuses 100 from which a user could select a suitable one for any of a variety of insertion guiding tasks.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. An apparatus for assisting an inclinometer in guiding a needle into a target location of a patient's body, the inclinometer including a planned needle guide trajectory stored in a computer-readable media readable by the inclinometer, the apparatus comprising:
   a top guide surface;
   a bottom guide surface, longitudinally spaced from the top guide surface by a guide body;
   an inclinometer-accepting slot extending laterally into the guide body and longitudinally spaced from both the top and bottom guide surfaces;
   at least one handle extending longitudinally upward from the top guide surface; and
   a plurality of needle guiding apertures extending through the guide body substantially perpendicularly to the top and bottom guide surfaces and selectively accepting at least a portion of the needle longitudinally therethrough, each needle guiding aperture of the plurality of needle guiding apertures having a different largest cross-sectional dimension, measured laterally, than the other needle guiding apertures of the plurality of needle guiding apertures.

2. The apparatus of claim 1, wherein the guide body includes a grasping segment having laterally spaced first and second grasping segment ends, the grasping segment being longitudinally bounded by the top and bottom guide surfaces, and
  a side arm extending orthogonally and laterally from a selected one of the first and second grasping segment ends, at least one of the plurality of needle guiding apertures extending through a portion of the guide body forming the side arm.

3. The apparatus of claim 2, wherein the side arm is a first side arm, and the guide body includes a second guide arm extending orthogonally and laterally from an other one of the first and second grasping segment ends, the first and second guide arms both extending in the same direction from the grasping segment.

4. The apparatus of claim 1, wherein at least one of the plurality of needle guiding apertures is a longitudinally extending slot providing laterally oriented access for the needle thereinto.

5. The apparatus of claim 1, including an anesthesia port extending obliquely through a portion of the guide body and in fluid communication with at least one of the plurality of needle guiding apertures at the bottom guide surface.

6. The apparatus of claim 1, including a device leveler extending longitudinally downward from the guide body, below the bottom guide surface.

7. The apparatus of claim 1, wherein the inclinometer includes an optical sensor, the apparatus including a contrast indicator for selective engagement with the needle, the contrast indicator being detectable with the optical sensor for assisting with guiding the needle into the target location at the planned needle trajectory.

8. The apparatus of claim 1, wherein the inclinometer-accepting slot is configured to concurrently contact at least three adjoining orthogonal sides of the inclinometer.

9. The apparatus of claim 1, wherein the inclinometer-accepting slot extends completely laterally through the guide body.

* * * * *